(12) United States Patent
Scaff

(10) Patent No.: US 8,601,614 B2
(45) Date of Patent: Dec. 10, 2013

(54) STRENGTHENING GLOVE

(76) Inventor: Clinton Scaff, Henderson, TN (US)

( * ) Notice: Subject to any disclaimer, the term of this patent is extended or adjusted under 35 U.S.C. 154(b) by 159 days.

(21) Appl. No.: 12/984,763

(22) Filed: Jan. 5, 2011

(65) Prior Publication Data
US 2012/0167272 A1 Jul. 5, 2012

(51) Int. Cl.
*A41D 19/00* (2006.01)
(52) U.S. Cl.
USPC ........................................ 2/160; 2/162; 2/163
(58) Field of Classification Search
USPC ......... 2/159, 160, 161.1, 161.2, 161.3, 161.4, 2/161.8, 162, 163, 169, 170; 482/44, 47, 482/48
See application file for complete search history.

(56) References Cited

U.S. PATENT DOCUMENTS

| | | | | |
|---|---|---|---|---|
| 883,761 A * | 4/1908 | Taylor | 294/25 |
| 1,486,006 A * | 3/1924 | Blom | 132/73 |
| 2,524,979 A * | 10/1950 | Kimbrell | 2/161.8 |
| 3,152,337 A * | 10/1964 | Barry | 2/159 |
| 3,347,547 A * | 10/1967 | Hynes | 482/47 |
| 3,408,657 A * | 11/1968 | Gallagher | 2/159 |
| 3,944,220 A * | 3/1976 | Fasano | 482/47 |
| 4,684,123 A * | 8/1987 | Fabry | 482/105 |
| 4,765,320 A * | 8/1988 | Lindemann et al. | 602/22 |
| 4,766,612 A * | 8/1988 | Patton, Sr. | 2/16 |
| 4,781,178 A * | 11/1988 | Gordon | 602/22 |
| 4,796,306 A * | 1/1989 | Mitchell | 473/205 |
| 4,830,360 A * | 5/1989 | Carr, Jr. | 482/47 |
| 4,867,246 A * | 9/1989 | Kiger | 172/370 |
| 4,881,275 A * | 11/1989 | Cazares et al. | 2/161.1 |
| 5,022,094 A * | 6/1991 | Hames et al. | 2/163 |
| 5,295,948 A * | 3/1994 | Gray | 602/5 |
| 5,373,585 A * | 12/1994 | Wiggins | 2/159 |
| 5,453,064 A * | 9/1995 | Williams, Jr. | 482/47 |
| 5,476,439 A * | 12/1995 | Robinson | 601/40 |
| 5,527,244 A * | 6/1996 | Waller et al. | 482/47 |
| 5,538,488 A * | 7/1996 | Villepigue | 482/47 |
| 5,608,912 A * | 3/1997 | Cumberland | 2/16 |
| 5,697,103 A * | 12/1997 | Wiggins | 2/159 |
| 5,782,516 A * | 7/1998 | Partida | 294/25 |
| 6,553,576 B1 * | 4/2003 | Knapp | 2/161.6 |
| 6,938,274 B2 * | 9/2005 | Addington et al. | 2/161.1 |
| 7,163,308 B2 * | 1/2007 | Ferrari et al. | 362/103 |
| 7,234,172 B1 * | 6/2007 | Hoelscher | 2/161.1 |
| 7,406,720 B2 * | 8/2008 | Hoelscher | 2/161.1 |
| 7,415,735 B2 * | 8/2008 | Erickson et al. | 2/163 |
| 7,601,130 B2 * | 10/2009 | Farrell et al. | 602/20 |
| 7,712,153 B2 * | 5/2010 | Adams, Jr. | 2/163 |
| 7,731,633 B1 * | 6/2010 | Williams | 482/47 |
| 7,891,831 B2 * | 2/2011 | Chen | 362/103 |

(Continued)

*Primary Examiner* — Alissa L Hoey
(74) *Attorney, Agent, or Firm* — Law Office of Jerry D. Haynes

(57) ABSTRACT

A strengthening glove comprising a glove which includes finger coverings, a thumb covering and a wrist cover; a finger attachment fastened to the finger coverings and the thumb covering; a finger guide attached to a base of the finger coverings; a wrist strap wrapped around the wrist cover, where the wrist strap secures the glove on the hand; a resistance strap, one for each finger covering and the thumb covering, where the resistance strap includes an elastic strip attached to a finger grip portion at one end and a wrist grip portion at an opposing end; wherein the resistance strap attaches to the glove by the finger grip portion engaging the finger attachment, the elastic strip passing through the finger guide and the wrist grip portion engaging to the wrist strap. The resistance strap creates tension against a backside of the hand to strengthen the hand during movement.

4 Claims, 3 Drawing Sheets

(56) References Cited

U.S. PATENT DOCUMENTS

| | | | |
|---|---|---|---|
| 7,892,194 B2* | 2/2011 | Farrell et al. | 602/21 |
| 8,028,347 B2* | 10/2011 | Chang | 2/161.1 |
| 8,209,775 B2* | 7/2012 | Makis | 2/162 |
| 2003/0195093 A1* | 10/2003 | White | 482/124 |
| 2004/0060095 A1* | 4/2004 | Bradbury | 2/159 |
| 2004/0098788 A1* | 5/2004 | Addington et al. | 2/161.1 |
| 2005/0114982 A1* | 6/2005 | Gremmert | 2/159 |
| 2006/0211964 A1* | 9/2006 | Farrell et al. | 602/5 |
| 2007/0072739 A1* | 3/2007 | Kaufman | 482/44 |
| 2007/0087901 A1* | 4/2007 | Brassil et al. | 482/44 |
| 2009/0281470 A1* | 11/2009 | Sandusky et al. | 602/5 |
| 2010/0192279 A1* | 8/2010 | Hunsicker | 2/161.2 |
| 2010/0234182 A1* | 9/2010 | Hoffman et al. | 482/8 |
| 2010/0311546 A1* | 12/2010 | Kupferman | 482/47 |

\* cited by examiner

STRENGTHENING GLOVE

BACKGROUND OF THE INVENTION

1. Field of the Invention

The present invention relates to an orthopedic glove that includes straps attached to the backside of the glove, from fingertip to wrist, to create resistance against the hand as a user opens and closes their fingers.

2. Description of Related Art

Individuals who suffer with hand injuries understand the significant challenges with rehabilitating the hand. Various methods are used to aid and improve the hand whether they are injections, medications, splints or extensive therapy. Physical therapy is commonly prescribed to help strengthen muscles, tendons and ligaments and to improve hand movements and dexterity. Hand rehabilitation is usually a tedious, time consuming and enduring process that takes commitment from the person to maintain their exercises. The person often becomes frustrated with the time commitment and repetition required for therapy.

Some gloves have been developed as therapeutic devices to assists a person trying to improve their hands. For example, U.S. Pat. No. 4,781,178 by Kevin M. Gordon discloses an orthopedic glove wherein the glove includes a set of splints attached to against the fingers and back of the hand to immobilize those areas. The splints may be warmed and adjustably tightened to assist a user suffering with arthritis by preventing their hands from curling and becoming too rigid.

Alternatively, U.S. Pat. No. 4,830,360 by Earnest F. Carr, Jr. discloses an orthopedic exercise glove wherein the glove includes springs attached along the finger portions of the glove to provide tension against the fingers. U.S. Pat. No. 5,538,488 by James C. Villepigue discloses an exercising glove wherein the glove includes a set of spring loaded cables running along the finger portions. The spring loaded cables resist the motions of the glove during closing to help strengthen the hand. A problem with these gloves is that they utilize springs to create the necessary tension. The springs may easily snap or break during use which may further injure the user's hand.

It would be beneficial in the art to provide a device that helps a user strengthen their hands using either bands or straps to provide tension against each individual finger. It would also be desirable in the art to provide a glove that includes guides attached to the glove to ensure that the straps remain in place when the user moves their hands.

SUMMARY OF THE INVENTION

An object of the present invention is to provide a strengthening glove for a user to strengthen their hands by providing a set of straps attached from fingertip to wrist wherein the straps provide tension against the fingers during movement.

Another object of the present invention is to provide a strengthening glove wherein the glove includes a set of finger guides and a hand guide to ensure that the straps remain against user's hand.

Another object of the present invention is to provide a strengthening glove with adjustable straps wherein the straps may be adjusted against the fingertips and wrist with hook and loop fasteners.

In view of the foregoing disadvantages inherent in the prior art, the present invention provides a strengthening glove comprising a glove which includes finger coverings, a thumb covering and a wrist cover; a finger attachment fastened to the finger coverings and the thumb covering; a finger guide attached to a base of the finger coverings; a wrist strap wrapped around the wrist cover, where the wrist strap secures the glove on the hand; and a resistance strap, one for each finger covering and the thumb covering, where the resistance strap includes an elastic strip attached to a finger grip portion at one end and a wrist grip portion at an opposing end; wherein the resistance strap attaches to the glove by the finger grip portion engaging the finger attachment, the elastic strip passing through the finger guide and the wrist grip portion engaging to the wrist strap. The resistance strap creates tension against a backside of the hand to strengthen the hand during movement.

These together with other aspects of the present invention, along with the various features of novelty that characterize the present invention, are pointed out with particularity in the claims annexed hereto and form a part of this present invention. For a better understanding of the present invention, its operating advantages, and the specific objects attained by its uses, reference should be made to the accompanying drawings and descriptive matter in which there are illustrated exemplary embodiments of the present invention.

BRIEF DESCRIPTION OF THE DRAWINGS

The advantages and features of the present invention will become better understood with reference to the following detailed description and claims taken in conjunction with the accompanying drawings, wherein like elements are identified with like symbols, and in which:

Like reference numerals refer to like parts throughout the description of several views of the drawings.

DETAILED DESCRIPTION OF THE DRAWINGS

The present invention relates to an orthopedic glove that includes straps attached to the backside of the glove, from fingertip to wrist, to create resistance against the hand as a user opens and closes their fingers. The present invention provides a strengthening glove to strengthen the user's hand muscles ligaments and tendons, to improve dexterity and facilitate finger and wrist extension. The strengthening glove is especially beneficial for user's who have hand injuries, arthritis, muscle weakness or nerve damage to help them strengthen their hands, loosens their joints, or rehabilitate the muscles after injury. When using the strengthening glove, the form fitting glove promotes dexterity that is conductive to both general labor and nimble manipulative hand work. The strengthening glove is conveniently lightweight and portable to ensure that it is readily available, and is appropriate for use at home, work or while traveling.

Figure 1:
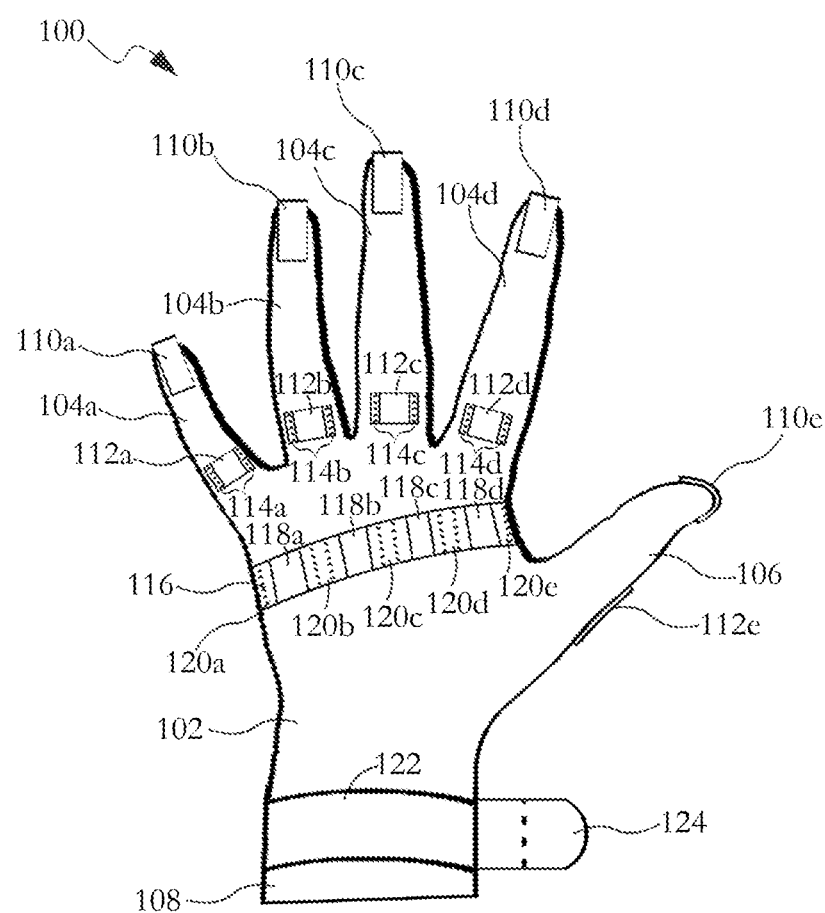
FIG. 1 depicts a perspective view of a strengthening glove in accordance with an exemplary embodiment of the present invention.

Tuning now descriptively to the drawings, referring to FIG. 1, a perspective view of a strengthening glove (100) is shown in accordance with an exemplary embodiment of the present invention. The strengthening glove (100) includes a glove (102) to envelope a hand of a user. The glove (102) may be a right hand glove or a left hand glove (as shown) and both may be available as a pair of strengthening gloves. Extending from a top portion of the glove (102) are a set of finger coverings (104a, 104b, 104c, 104d) [hereinafter referred to as finger covering (104)] to cover a set of fingers (hereinafter fingers) of the user. Along a side portion of the glove (102) is a thumb covering (106) to cover the user's thumb. Along a lower portion of the glove (102) is a wrist cover (108) that wraps around the user's wrist. The glove (102), the finger coverings (104), the thumb covering (106) and the wrist cover (108) are all made out of the same material for example neoprene, cotton, wool, nylon and other materials commonly used in the art for athletic or orthopedic gloves. Additionally, the glove (102) is lightweight and portable for easily storage and access.

At a tip of the finger covering (104) and the thumb covering (106) is a set of finger attachments (110a, 110b, 110c, 110d, 110e) [hereinafter referred to as finger attachments (110)], a single finger attachment (110) for each finger covering (104). The finger attachments (110) are covered in loop material from hook and loop fasteners so that the finger attachment (110) is soft to the touch. The finger attachments (110) essentially cover the tip of the finger covering (104) or the nail portion of the finger, and may wrap around to the opposing side of the finger. The finger attachments (110) are no wider than the finger coverings (104) so that the finger attachments (110) do not interfere with the movements of the fingers.

At the base of the finger coverings (104) and the thumb covering (106) are a set of finger guides (112a, 112b, 112c, 112d, 112e) [hereinafter finger guides (112)] that attach to the finger coverings (104). A single finger guide (112) is attached to each finger covering (104) and the thumb covering (106). The finger guides (112) are attached to the finger coverings (104) with a plurality of stitched ends (114a, 114b, 114c, 114d) [hereinafter stitched ends (114)] that run parallel to the finger coverings (104). The finger guides (112) are open at a top portion and a bottom portion and sewn against the finger coverings (104) with the stitched ends (114) on each side. The finger guides (112) are in line with the finger attachments (110) so that if an invisible line were drawn from the center of the finger attachment (110) to the center of the finger guides (112) it would be relatively straight.

Along a backhand portion of the glove (102) may be a hand guide (116) that runs between the finger guides (112) and the wrist cover (108). The hand guide (106) extends from between where the thumb and forefinger meet to an outer portion of the glove (102) by the pinky. The hand guide (106) may have a plurality stitched ends (120a, 120b, 120c, 120d, 120e) [hereinafter stitched ends (120)] to fasten the hand guide (106) to the glove (102). Between the stitched ends (120) are a set of openings (118a, 118b, 118c, 118d) [hereinafter openings (118)]. The openings (118) align with the coordinating finger coverings (104) wherein the finger covering (104a) aligns with the opening (118a), the finger covering (104b) aligns with the opening (118b) and so forth.

On the wrist cover (108) is a wrist strap (122). The wrist strap (122) encircles the user's wrist to fasten the glove (102) on the user's hand. Along the front portion of the wrist strap (122) is a strip of loop material from a hook and loop fastener. At an end of the wrist strap (122) is a securing means (124). The securing means (124) may be a hook and loop fastener, a snap, a button or the like. The securing means (124) engages the wrist strap (122) to tighten and secure the wrist strap (122) around the wrist.

Figure 2:
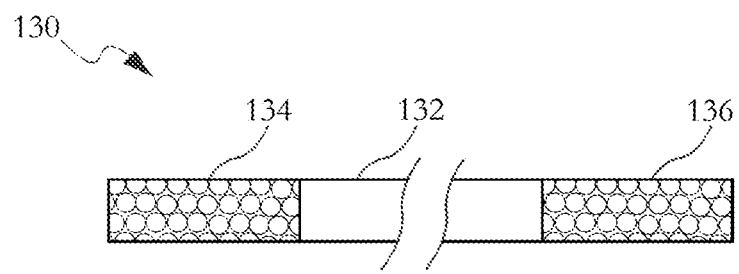
FIG. 2 depicts a perspective view of a resistance strap in accordance with an exemplary embodiment of the present invention.

Referring now to FIG. 2, a perspective view of a resistance strap (130) is shown in accordance with an exemplary embodiment of the present invention. The resistance strap (130) includes an elastic strip (132) that attaches to a pair of grip portions (134, 136). The pair of grip portions (134, 136) may be separated into a finger grip portion (134) that attaches to the elastic strip (132) at one end and a wrist grip portion (136) that attaches to the elastic strip (132) at an opposing end. The elastic strip (132) may be a long narrow piece of elastic that enables the finger grip portion (134) and the wrist grip portion (136) to stretch away and towards each other. The pair of grip portions (134, 136) may be sewn or glued to the elastic strip (132) for a permanent attachment. Covering the pair of grip portions (134, 136) are pieces of hooks material from a hook and loop fastener.

Figure 3:
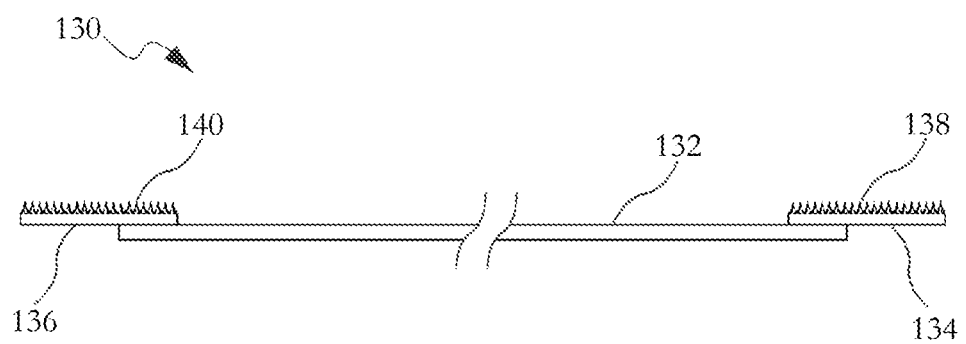
FIG. 3 depicts a side view of a resistance strap in accordance with an exemplary embodiment of the present invention.

Referring to FIG. 3 a side view of the resistance strap (130) is shown in accordance with an exemplary embodiment of the present invention. The elastic strip (132) is shown behind the pair of grip portions (134, 136). On the front side of the pair of grip portions (134, 136) are the pieces of hook material (138, 140). The finger grip portion (134) has a finger hook material (138) attached, whereas the wrist grip portion (134) has a wrist hook material (140).

Figure 4:
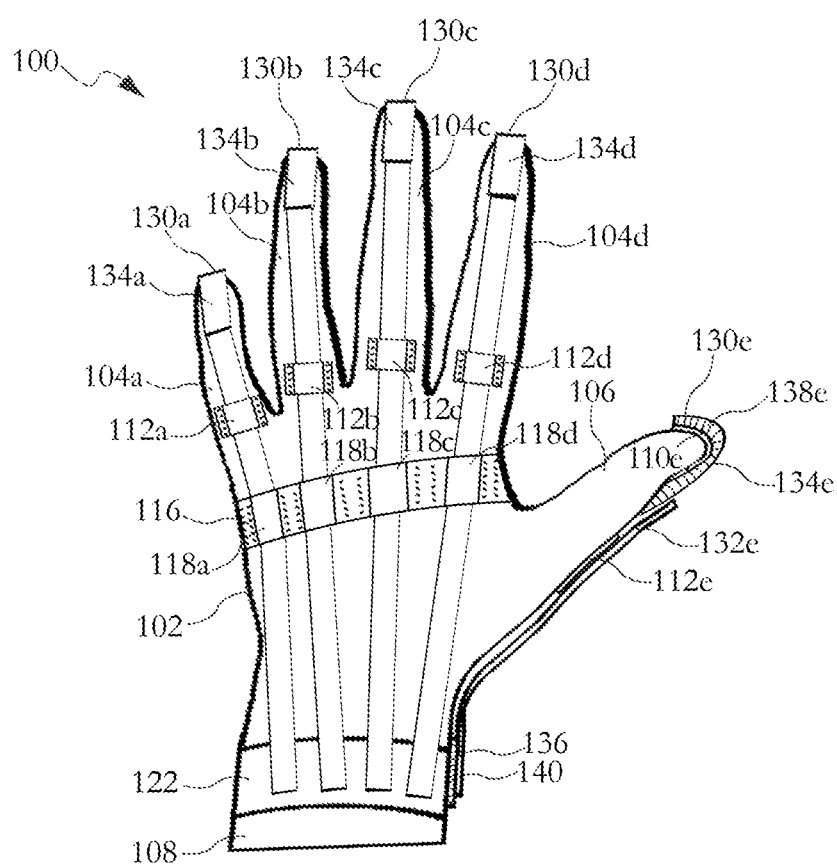
FIG. 4 depicts a strengthening glove with a set of resistance straps in accordance with an exemplary embodiment of the present invention.

FIG. 4 depicts the strengthening glove (100) with a set of resistance straps (130a, 130b, 130c, 130d, 130e) [hereinafter resistance straps (130)] are shown in accordance with an exemplary embodiment of the present invention. The resistance straps (130) are attached by engaging the finger grip portion (134) around the finger attachments. The finger grip portion (134) remains in place when the finger hook material (138) engages the sections of loop material on the finger attachments (110) to create a complete hook and loop fastener. After attaching the finger grip portion (134), the wrist grip portion (136) is threaded through the finger guide (112) and then threaded through the following opening (118) in the hand guide (116). For example, when using the resistance strap (130a), the finger grip portion (134a) fastens to finger attachment (110a), threads through finger guide (112a) and then through opening (118a). The finger guide (112) and the hand guide (116) ensure that the resistance straps (130) remain against the glove (102) while the hand opens and closes.

The thumb resistance strap (130e) attaches a little differently because there is no opening in the hand guide (116) for the thumb. Instead the resistance strap (130e) for the thumb only threads through the finger guide (112e). Finally, the wrist grip portion (136e) of the resistance strap (130e) is connected to the strip of loop material attached to the wrist strap (122).

During use, the strengthening glove (100) combined with the resistance straps (130) provides therapeutic tension against the user's fingers. In order for the user to close their hand they must overcome the tension in the resistance straps (130) thereby strengthening and rehabilitating the hand. The tension along the resistance strap (130) may be adjusted by tightening and loosening the finger grip portions (134) against the finger attachments (110), or the wrist grip portions (136) against the wrist strap (122) As the user becomes stronger they may increase the tension on the resistance strap (130) for a more intense strengthening session.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The exemplary embodiment was chosen and described in order to best explain the principles of the invention and its practical application, to thereby enable others skilled in the art to best utilize the invention and various embodiments with various modifications as are suited to the particular use contemplated.

What is claimed is:

1. A strengthening glove comprising:
   a glove to envelope a hand, where said glove includes a set of finger coverings, a thumb covering and a wrist cover;
   a finger attachment fastened to a tip of each of said set of finger coverings and said thumb covering, where said finger attachments are covered in a loop material from a hook and loop fastener;
   a set of finger guides, where each finger guide is attached to a base of each of said set of finger coverings; and where each finger guide is open at a top portion and a bottom portion;
   a wrist strap wrapped around said wrist cover, where said wrist strap secures said glove around said hand, and where said wrist strap is covered in a loop material from a hook and loop fastener;
   a hand guide that stretches across said backside of said hand, between said finger guide and said wrist strap, where said hand guide includes a set of openings to coordinate with said set of finger covering; and
   a resistance strap, one for each finger covering and said thumb covering, where said resistance strap includes an elastic strip attached to a finger grip portion, covered in a hook material from a hook and loop fastener, at one end and a wrist grip portion, covered in a hook material from a hook and loop fastener, at an opposing end;
   wherein said resistance strap attaches to said glove by said finger grip portion engaging said finger attachment, said elastic strip passing through said opening in said finger guide and then through said set of openings in said hand guide, and said wrist grip portion engaging to said wrist strap and where said resistance strap creates tension against a backside of said hand for when said hand opens and closes; and
   wherein said hook material of said resistance straps enable adjustments against said loop material of said finger attachments and said wrist strap by repositioning one of at least said finger grip portion and said wrist grip portion.

2. The strengthening glove according to claim 1, wherein said finger guide and said hand guide are secured to said glove with a plurality of stitched ends.

3. The strengthening glove according to claim 1, wherein said wrist strap includes a securing means to prevent said glove from coming off said hand.

4. The strengthening glove according to claim 3, wherein said securing means includes one of at least a hook and loop fastener, a snap and a button.

\* \* \* \* \*